Figure 1:
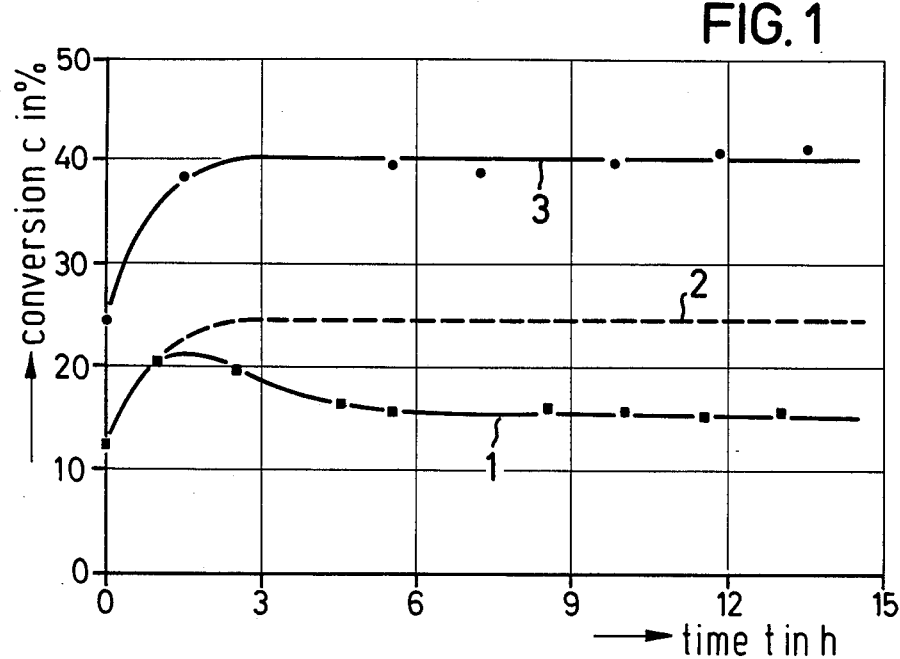

United States Patent [19]

Tiltscher et al.

[11] Patent Number: 4,721,826
[45] Date of Patent: Jan. 26, 1988

[54] PROCESS FOR RESTORING OR MAINTAINING THE ACTIVITY OF HETEROGENEOUS CATALYSTS FOR REACTIONS AT NORMAL AND LOW PRESSURES

[75] Inventors: Helmut Tiltscher, Munich; Helmut Wolf, Garching; Joachim Schelchshorn; Kurt Dialer, both of Munich, all of Fed. Rep. of Germany

[73] Assignee: Hoechst Aktiengesellschaft, Frankfurt am Main, Fed. Rep. of Germany

[21] Appl. No.: 849,131

[22] Filed: Apr. 7, 1986

Related U.S. Application Data

[60] Division of Ser. No. 731,348, May 6, 1985, Pat. No. 4,605,811, which is a continuation of Ser. No. 268,387, May 9, 1981, abandoned.

[30] Foreign Application Priority Data

May 31, 1980 [DE] Fed. Rep. of Germany ....... 3020698

[51] Int. Cl.$^4$ .......................... C07C 2/68; B01J 21/20; B01J 29/38
[52] U.S. Cl. ...................................... 585/467; 502/20; 502/34; 585/468
[58] Field of Search ...................... 502/34, 20; 585/467

[56] References Cited

U.S. PATENT DOCUMENTS

| 2,353,552 | 7/1944 | Prennan | 585/670 |
| 4,291,185 | 9/1981 | Kaeding | 585/467 |

FOREIGN PATENT DOCUMENTS

| 2853065 | 6/1980 | Fed. Rep. of Germany | 502/34 |
| 3020698 | 5/1982 | Fed. Rep. of Germany | 502/20 |

Primary Examiner—P. E. Konopka
Attorney, Agent, or Firm—Curtis, Morris & Safford

[57] ABSTRACT

By the process of the present invention the activity of heterogeneous catalysts for reactions at normal and low pressures is restored or maintained. These catalysts can lose their activity as a result of the deposition, physisorption or chemisorption of organic or inorganic deactivating substances which are carried over into the reaction system or are formed as the result of side reactions in a chemical synthesis carried out with the aid of the catalyst. The activity is restored or maintained by using a pressure greater than the critical pressure of the fluid phase and a temperature higher than or equal to the critical temperature of the fluid phase. In this process, the pressure and temperature are applied for a period such that the deactivating substances are either removed from the catalyst or are not initially deposited thereon or absorbed or formed.

9 Claims, 4 Drawing Figures

PROCESS FOR RESTORING OR MAINTAINING THE ACTIVITY OF HETEROGENEOUS CATALYSTS FOR REACTIONS AT NORMAL AND LOW PRESSURES

This application is a division of application Ser. No. 731,348, filed May 6, 1985, now U.S. Pat. No. 4,605,811, which is a continuation of application Ser. No. 268,387, filed on May 29, 1981, now abandoned.

The invention relates to a process for restoring or maintaining the activity of heterogeneous catalysts for reactions at normal and low pressures, which can lose their activity as a result of the deposition, physisorption or chemisorption of organic or inorganic substances which are carried over into the reaction system or are formed in a chemical synthesis as a consequence of side reactions.

Losses of activity in heterogeneously catalyzed syntheses are of very great practical importance. A loss of catalytic activity results in decreased production output, and a decrease also by virtue of the deterioration in yield and selectivity. In addition to its specific catalytic action, and to the high mechanical strength required of a catalyst in practical operation, an activity which remains constant for as long a period as possible has, above all, a decisive effect on the cost efficiency of a process. Generally the cause of a catalytic loss in activity, is aside from electronics effects, considered to be the result of a reduction in the number of active sites on the internal or external surface of the catalyst which is primarily due to one of the following.

1. Poisoning caused by specific catalyst poisons which have been carried over into the reaction system and which are so strongly physisorbed or chemisorbed on the active centers that they can no longer be desorbed sufficiently fast under the synthesis conditions normally employed.
2. The deposition on the active centers of the external or internal surface of the catalyst ("fouling") of sparingly volatile substances which (a) are carried over into the reaction system or (b) are formed as the result of undesired parallel reactions or secondary reactions.
3. Aging caused by structural changes on the catalytically active surface (for example sintering processes, recrystallization processes, transport reactions and the like).

The art contains numerous processes, mostly very involved processes, for prolonging the life of heterogeneous catalysts. For example, additional process stages are frequently used, such as a preliminary purification of the starting materials or process gases or circulatory gas washing, in order to suppress poisoning or deposition caused by substances carried over into the reaction system. In general, however, effects of this type cannot be excluded completely, above all because of the high costs associated therewith. Similarly, deposits are formed because of side reactions industrial syntheses in which reactions are generally carried out in highly concentrated systems and under drastic operating conditions and with optional conversions in order to achieve high space-time yields.

In many catalytic syntheses in organic chemistry, particularly in petrochemistry, high-molecular polymerization products which are rich in carbon are deposited on the catalysts. This is described quite generally as coking, but the rate and the extent of the deposition of coke are very different in the various processes. In catalytic cracking, for example, it is necessary after as short a period as hours or fractions of an hour to reactivate the catalyst, that is to say to restore its activity, so that the process is frequently carried out in several reactors which are operated alternately. If the catalyst is in a fixed bed, the reactivation is in most cases carried out by slowly burning off the coke, in which process it is necessary to ensure carefully that a temperature limit harmful to the catalyst is not exceeded and that aging as described above caused by heat does not take place. Moving bed and fluidized bed catalysts are frequently reactivated by withdrawing part of the catalyst from the reactor and calcining it in a regenerator, the size of which frequently exceeds that of the reactor itself. In this respect, the desire to burn off coke as quickly as possible since rapid burning off can be carried out even in a small regenerator must be balanced by the requirement that the coke must be burnt off gently.

Kinetic research described in the literature concerning the mechanism of the deactivation of heterogeneous contact catalysts by fouling resulting from side reactions is chiefly concerned with the formation of coke in cracking reactions. It is known from these investigations that the content of aromatics and olefins has a great effect on the extent and rate of coking. Particularly in the case of reactions involving olefins on acid contact catalysts, polymerization reactions are suggested as the origin of the deactivation process. Because of their high molecular weight and their fairly low volatility, the oligomers initially formed are no longer desorbed from the contact catalyst at the same rate at which they are formed and they cause deposition of high-molecular material through further reactions.

It was indeed already known that increasing the reaction temperature can promote the desorption and the detachment of sparingly volatile substances in some cases. In general, however, the advantages of improved desorption conditions at higher temperatures are eliminated by the disadvantages of an increased reaction rate for side reactions. In regard to the effect of pressure in deactivation processes, reference is made in the literature to the fact that a higher pressure promotes sorption processes and thus accelerates the loss of activity caused by the deposition, physisorption or chemisorption of deactivating substances.

It has been found that the removal of such substances from the catalyst or prevention of initial deposition or formation can be improved significantly in accordance with the present invention.

Substances which have already been deposited or absorbed are removed from the catalyst in a very gentle manner and are removed from the reaction system. If supercritical reaction conditions are selected from the outset, compounds which have been carried over into the reaction system or which are formed in the course of side reactions are prevented from becoming deposited or absorbed and are discharged continuously.

The process according to the invention is relevent, not only in the case of high-molecular deposits which are rich in carbon, but also in the case of catalyst poisons having a specific action which are physisorbed or chemisorbed on the reactive centers. The pressures to be used are frequently already within the pressure range from approx. 50 to approx. 150 bars which is of industrial interest. In cases where deposited products can react further (for example polymerize), it is possible for such a further reaction to be completely suppressed.

The more rapidly the reactivation process is to be effected and the more sparingly volatile the deactivating substances or the more strongly they are physisorbed or chemisorbed, the higher is the pressure required. This procedure also makes possible partial removal from the catalyst, whereby the conditions can be adjusted so that, for example, catalytically active substances (for example noble metals) which have been deposited on a support material, remain on the catalyst and only deactivating substances are removed. The procedure can be carried out by choosing a temperature equal to or higher than the critical temperature ($T \geq T_c$) and varying the pressure ($p > p_c$), or by selecting a pressure greater than the critical pressure of the fluid phase ($p > p_c$) and varying the temperature ($T > T_c$).

Compared with known methods for reactivating heterogeneous catalysts, the process according to the invention provides the following substantial advantages:

(A) It is carried out under relatively mild conditions. Compared with the method of reactivating catalysts for calcining, the risk of deactivating the catalyst through aging is avoided.

(B) The restoration or maintenance of the activity is effected through the fluid reaction phase itself. In this way no foreign substances are carried over into the reaction system, as is the case, for example, with extractive purification.

(C) The process can be carried out "in situ" and does not cause any lengthy periods of down-time.

(D) The process according to the invention makes it possible to effect a fractional removal of deactivating substances.

If a pressure which is at least equal to the critical pressure and a temperature which is at least equal to the critical temperature of the fluid reaction phase are applied throughout the duration of the reaction, this produces the following additional advantages:

(E) The heterogeneous catalyst employed in a chemical syntheses can be operated for very long reaction times at a constant catalytic activity.

(F) If the catalytic activity remains constant, it is possible to employ considerably more drastic conditions in the catalytic reaction and thus achieve higher space-time yields.

If the critical pressure or the critical temperature of the fluid phase have particularly high values, it is frequently advisable to reduce these values by adding auxiliary substances. Examples of suitable auxiliary substances are hydrocarbons, such as methane, propane, butane or pentane, or carbon dioxide or nitrogen or argon.

The process according to the invention is applicable, for example, to the isomerization of 1-hexene on oxide contact catalysts such as $\eta$-$Al_2O_3$, the alkylation of benzene with olefins, such as ethylene, propene, butene, n-hexene or cyclohexene, on oxide contact catalysts such as $\eta$-$Al_2O_3$ or zeolites, and to isomerization reactions of saturated hydrocarbons and to cracking, dehydrogenation, halogenation and sulfonation reactions. Examples of other suitable fields of application are reactions in which addition or polymerization reactions result in undesirable higher-molecular compounds, such as oxyalkylation reactions of alcohols, phenols or amines by means of ethylene oxide or propylene oxide.

The following examples illustrate the invention:

EXAMPLE 1

(Catalyst deactivation caused by the deposition of sparingly volatile substances formed as the result of parallel or secondary reactions; FIG. 1)

7.5 g of freshly prepared catalyst ($\eta$-$Al_2O_3$; particle diameter: 0.6–0.75 mm; catalytically active specific surface area: 4.95 $m^2$/g) are introduced, in an activated state, into a high-pressure differential circulating reactor having a fixed bed arrangement for the catalyst. 1-Hexene containing 0.016 mole/l of 2-chlorohexane is fed continuously into the reactor at a pressure of 15 bars and a temperature of 250° C. (average residence time: $1.08 \times 10^5$ s.g/mole; circulation factor: approx. 100).

As shown by curve 1 in FIG. 1, under these conditions, with a gaseous fluid phase, the 24% conversion of 1-hexene expected from theory (curve 2) is not achieved after stable operating conditions have been established in the circulating reactor (approx. 4 hours=four times the average residence time). The resulting course of the reaction is typical of a reaction on which a deactivation process is superimposed. In the colorless solution of product which emerges, only the isomeric hexenes (1-hexene, cis-2-hexene, trans-2-hexene and trans-3-hexene) can be detected by gas chromatography (GC) and mass spectroscopy (MS) and by analysis by capillary gas chromatography.

Establishing supercritical conditions by increasing the pressure to 500 bars, after an operating time of about 14 hours, produces an immediate dark brown discoloration of the product solution, which gradually becomes pale again. The conversion after this reactivation phase corresponds to the figure to be expected on the basis of theory and, as illustrated in curve 3, no decrease in the catalytic activity is observed under these conditions, even over extremely long operating times, in spite of the considerably higher reaction rate which is produced.

In the product solution with emerges with a dark brown discoloration, it is possible to detect by GC/MS methods the corresponding hexene oligomers ($C_{12}$, $C_{18}$, $C_{24}$... compounds) which, in the isomerization reaction employing a gaseous reactant phase, remain on the catalyst by virtue of their low volatility and cover the active centers. A constant, small quantity of hexene oligomers can be determined in the product solution which emerges after the reactivation phase.

EXAMPLE 2

Figure 2:
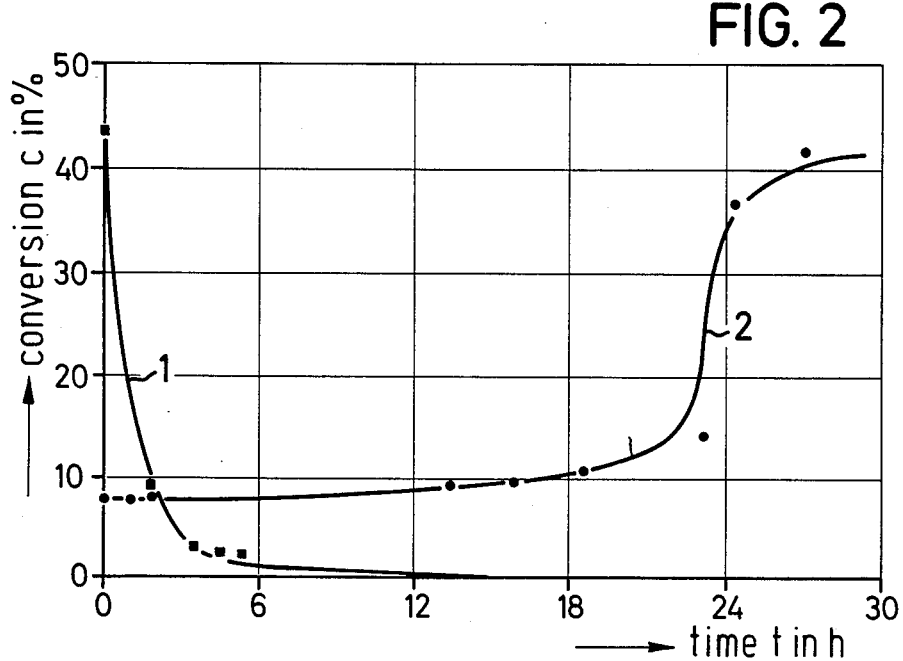

(Catalyst deactivation caused by a specific catalyst poison; FIG. 2)

A $6.4 \times 10^{-2}$ molar solution of pyridine in 1-hexene is fed continuously for about 12 hours into a differential circulating reactor having a fixed bed arrangement corresponding to Example 1, at a temperature of 45° C. and a pressure of 50 bars. After the active acid centers of the catalyst have been poisoned by pyridine, the conversion in the isomerization reaction rapidly falls nearly to zero, corresponding to the deactivation illustrated in curve 1 of FIG. 2.

The catalyst can no longer be reactivated, even if very long operating times are employed, by increasing the temperature to 220° C. and the pressure to 500 bars, that is to say at sub-critical conditions and a liquid fluid phase.

After increasing the temperature further to 250° C., with the pressure unchanged at 500 bars, that is to say with a supercritical fluid phase, when stable operating conditions have been established, the conversion achieved is initially only approx. 8% and this increases slowly with time, in accordance with curve 2, until finally, after about 24 hours, the original figure of 40% conversion is re-established.

Pyridinium hydrochloride can be detected in the product solution which emerges during the reactivation phase.

EXAMPLE 3

Figure 3:
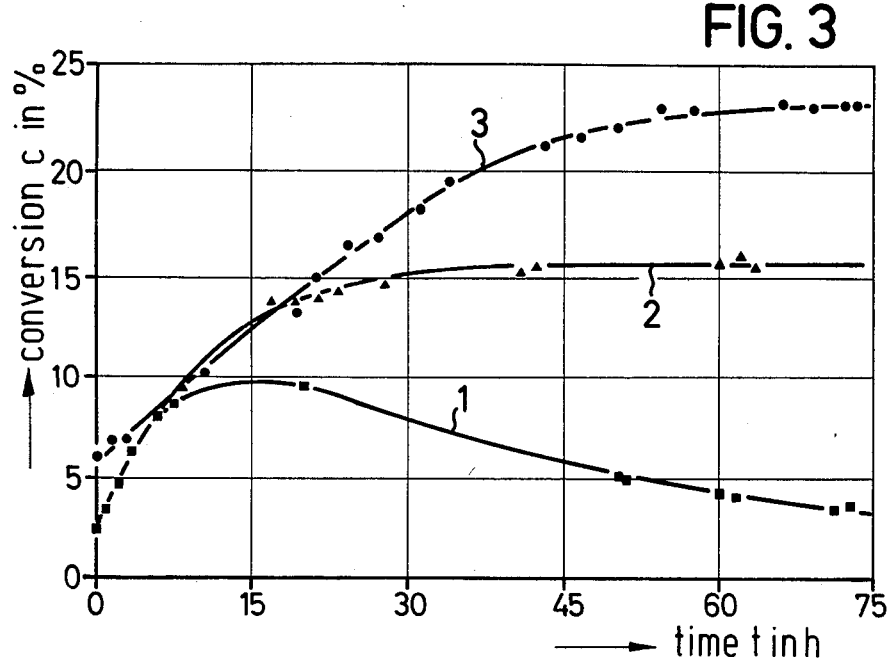

(Catalyst deactivation caused by sparingly volatile inorganic substances carried over into the reaction system; FIG. 3)

1-Hexene containing small quantities of a lubricant based on $MoS_2$ is introduced into a differential circulating reactor having a fixed bed arrangement for the catalyst corresponding to Example 1. A loss in conversion corresponding to curve 1 in FIG. 3 is determined for the hexene isomerization reaction at a temperature of 220° C. and a pressure of 500 bars and a liquid fluid phase. Deactivation of the catalyst through deposition of the lubricant is superimposed on the isomerization reaction. Under these conditions, the catalyst can no longer be reactivated even after extremely long operating times. Increasing the temperature to 240° C., with the pressure unchanged at 500 bars, that is to say with a supercritical fluid phase, produces the reactivation shown in FIG. 3. The catalyst recovers its full activity after about 75 hours. Curve 2 for the isomerization reaction in the absence of deactivation is obtained using the catalyst which has been reactivated in this way.

EXAMPLE 4

Figure 4:
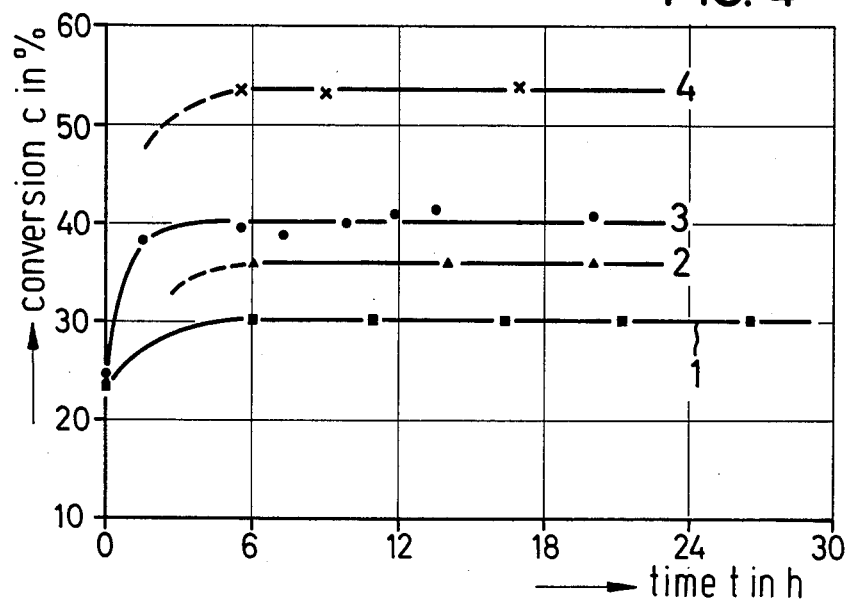

(Maintaining the activity of the catalyst in a synthesis as the result of selecting supercritical reaction conditions; FIG. 4)

A freshly prepared catalyst is introduced, in an activated state corresponding to Example 1, into a differential circulating reactor having a fixed bed arrangement for the catalyst. After stationary conditions have been established at a temperature of 250° C. and a pressure of 75 bars (curve 1), 250 bars (curve 2), 500 bars (curve 3) or 850 (curve 4), a conversion which remains constant even over extremely long experimental periods is obtained for the isomerization of 1-hexene.

Small quantities of hexene oligomers can be detected by GS/MS methods in the product solutions which emerge.

EXAMPLE 5

(Catalyst deactivation caused by the deposition of sparingly volatile substances formed in parallel or secondary reactions)

5 g of freshly prepared catalyst, in an activated state corresponding to Example 1, are introduced into a differential circulating reactor having a fixed bed arrangement for the catalyst. Benzene, cyclohexene and 2-chlorohexane in a molar ratio of 600:200:1 are fed continuously into the reactor at a pressure of 15 bars and a temperature of 305° C.

Under these conditions, in which the fluid phase is gaseous, the conversion efficiency, relative to the benzene employed, achieved after stationary operating conditions have been established in the circulating reactor (approx. 4 hours=four times the average residence time) is not constant. Deactivation of the catalyst is superimposed on the alkylation reaction. After an operating time as short as 20 hours, the degree of conversion falls by approx. 30% from the maximum figure obtainable.

Increasing the pressure to 150 bars to give a supercritical fluid phase produces an immediate dark brown discoloration of the product solution, which gradually becomes pale again. The conversion established after the reactivation phase at the higher pressure and with the operating conditions otherwise identical, remains constant over long periods of operation; it is about 40% higher than the conversion before reactivation.

We claim:

1. A process for reactivating or maintaining the activity of an oxide contact catalyst useful for catalytic alkylation of benzene with an olefin at atmospheric or low pressure wherein the oxide contact catalyst tend to decrease in activity by deposition, physisorption or chemisorption of organic or inorganic deactivating substances present at the start of said catalytic alkylation or formed during said alkylation, which comprises conducting said catalytic alkylation at an operating pressure above the critical pressure and a temperature of at least equal to the critical temperature of the fluid benzene and olefin reactants for a period of time at least sufficient to remove any deactivating substances on said catalyst and to avoid formation, deposition, physisorption or chemisorption thereof on said catalyst.

2. The process of claim 1 wherein said operating pressure and temperature are selected to effectuate fractional removal of deactivating substances present on said catalyst.

3. The process of claim 1 wherein the effective critical pressure and temperature of said benzene and olefin reactants is lowered by addition of an effective amount of a compatible reaction auxiliary inert to said catalytic alkylation.

4. The process of claim 1 wherein said catalyst is $\eta$-$Al_2O_3$.

5. The process of claim 1 wherein said catalyst is a zeolite.

6. A process for reactivating or maintaining the activity of an oxide contact catalyst useful for catalytic alkylation of benzene with an olefin at atmospheric or low pressure wherein the oxide contact catalyst tends to decrease in activity by deposition, physisorption or chemisorption of organic or inorganic substances present at the start of said catalytic alkylation or formed during said alkylation, which comprises conducting said catalytic alkylation at an operating pressure and temperature at least equal to the critical pressure and temperature of the fluid benzene and olefin reactants for a period of time at least sufficient to remove any deactivating substances on said catalyst and to avoid formation, deposition, physisorption or chemisorption thereof on said catalyst.

7. The process of claim 6 wherein the effective critical pressure and temperature of said benzene and olefin reactants is lowered by addition of an effective amount of a compatible reaction auxiliary inert to said catalytic alkylation.

8. The process of claim 6 wherein said catalyst is $\eta$-$Al_2O_3$.

9. The process of claim 6 wherein said catalyst is a zeolite.

* * * * *

UNITED STATES PATENT AND TRADEMARK OFFICE
CERTIFICATE OF CORRECTION

PATENT NO. : 4,721,826

DATED : January 26, 1988

INVENTOR(S) : Tiltscher et al.

It is certified that error appears in the above-identified patent and that said Letters Patent is hereby corrected as shown below:

On the cover page of the patent, delete "[73] Assignee: Hoechst Aktiengesellschaft, Frankfurt am Main, Fed. Rep. of Germany".

Signed and Sealed this

Fourteenth Day of March, 1989

*Attest:*

DONALD J. QUIGG

*Attesting Officer*  *Commissioner of Patents and Trademarks*